United States Patent
Cho et al.

(10) Patent No.: US 10,918,709 B2
(45) Date of Patent: *Feb. 16, 2021

(54) IMMUNE MODULATOR AND VACCINE COMPOSITION CONTAINING THE SAME

(71) Applicant: EYEGENE INC., Seoul (KR)

(72) Inventors: Yang Je Cho, Seoul (KR); Kwangsung Kim, Gyeonggi-do (KR); Na Gyong Lee, Seoul (KR); Shin Ae Park, Seoul (KR)

(73) Assignee: EYEGENE INC., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/345,699

(22) PCT Filed: Oct. 30, 2017

(86) PCT No.: PCT/KR2017/012050
§ 371 (c)(1),
(2) Date: Apr. 26, 2019

(87) PCT Pub. No.: WO2018/080252
PCT Pub. Date: May 3, 2018

(65) Prior Publication Data
US 2019/0290749 A1    Sep. 26, 2019

(30) Foreign Application Priority Data

Oct. 31, 2016  (KR) .................. 10-2016-0142703
Jun. 23, 2017  (KR) .................. 10-2017-0079762

(51) Int. Cl.
*A61K 39/12* (2006.01)
*A61P 31/12* (2006.01)
*A61K 39/39* (2006.01)
*C08B 37/00* (2006.01)
*A61K 31/739* (2006.01)
*A61K 39/002* (2006.01)
*A61K 39/00* (2006.01)
*A61K 39/295* (2006.01)

(52) U.S. Cl.
CPC ............ *A61K 39/12* (2013.01); *A61K 31/739* (2013.01); *A61K 39/00* (2013.01); *A61K 39/002* (2013.01); *A61K 39/295* (2013.01); *A61K 39/39* (2013.01); *A61P 31/12* (2018.01); *C08B 37/006* (2013.01); *A61K 2039/522* (2013.01); *A61K 2039/5254* (2013.01); *A61K 2039/6087* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 7,507,802 B2 * | 3/2009 | Ahn ..................... | A61K 31/739 536/23.1 |
| 8,945,590 B2 * | 2/2015 | Fairman ............. | A61K 39/0208 424/184.1 |
| 2006/0166923 A1 | 7/2006 | Ahn et al. | |
| 2009/0074800 A1 * | 3/2009 | Nakatsura .......... | C07K 14/4748 424/185.1 |
| 2019/0255171 A1 * | 8/2019 | Cho ..................... | A61K 9/1272 |

FOREIGN PATENT DOCUMENTS

| | | |
|---|---|---|
| EP | 2444103 A1 | 4/2012 |
| JP | 2006506399 A | 2/2006 |
| JP | 2012530488 A | 12/2012 |
| KR | 20030090897 A | 12/2003 |
| KR | 100456681 B1 | 11/2004 |
| KR | 20060117387 A | 11/2006 |
| KR | 100740237 B1 | 7/2007 |
| KR | 20120013260 A | 2/2012 |
| KR | 101509456 B1 | 4/2015 |
| WO | WO2004039413 A1 | 5/2004 |
| WO | WO2006121232 A1 | 11/2006 |

OTHER PUBLICATIONS

Muller-Loennies et al., "Chemical structure of the core region of *Escherichia coli* J-5 lipopolysaccharide" European Journal of Biochemistry vol. 224 pp. 751-760 (Year: 1994).*
Mueller-Loennies et al., "Neutralizing and cross-reactive antibodies against enterobacterial lipopolysaccharide" International Journal of Medical Microbiology vol. 297 pp. 321-340 (Year: 2007).*
Heinrichs et al., "The Assembly System for the Outer Core Portion of R1- and R4-type Lipopolysaccharides of *Escherichia coli*" The Journal of Biological Chemistry vol. 273 No. 45 pp. 29497-29505 (Year: 1998).*
Whitfield et al., "Assembly of the R1-type core oligosaccharide of *Escherichia coli* lipopolysaccharide" Journal of Endotoxin Research vol. 5 No. 3 pp. 151-156 (Year: 1999).*
Akira, S., et al., "Pathogen Recognition and Innate Immunity", "Cell", Feb. 24, 2006, pp. 783-801, vol. 124.
Bello, G., et al., "The Influence of Rough Lipopolysaccharide Structure on Molecular Interactions with Mammalian Antimicrobial Peptides", "Biochimia et Biophysica Acta", 2016, pp. 197-209, vol. 1858.

(Continued)

*Primary Examiner* — Eric Olson
(74) *Attorney, Agent, or Firm* — Hultquist, PLLC; Steven J. Hultquist

(57) ABSTRACT

The present invention relates to an immune modulator having a novel structure, and an immunologic adjuvant composition containing the same and, more specifically, to an modulator, which is a lipopolysaccharide (LPS) analog having reduced toxicity, and a use thereof. The immune modulator of the present invention exhibits immune enhancement effects by having excellent innate immunity and ability to induce an adaptive immune response to a specific pathogen, and is very safe by having low toxicity. In addition, a vaccine containing the immune modulator of the present invention contains both an immune modulator and an alum, thereby improving immune enhancement effects compared with when using only the immune modulator.

9 Claims, 12 Drawing Sheets
(5 of 12 Drawing Sheet(s) Filed in Color)

(56) References Cited

OTHER PUBLICATIONS

Clifton, L., et al., "Asymmetric Phospholipid: Lipopolysaccharide Bilayers; a Gram-Negative Bacterial Outer Membrane Mimic", "Journal of the Royal Socieity Interface", 2013, pp. 1-11, vol. 10.
Katz, S., et al., "Deacylation of Lipopolysaccharide in Whole *Escherichia coli* During Destruction by Cellular and Extracellular Components of a Rabbit Peritoneal Inflammatory Exudate", "The Journal of Biological Chemistry", 1999, pp. 36579-36584, vol. 274, No. 51.
Raetz, C., et al., "Lipopolysaccharide Endotoxins", "Annu Rev Biochem", 2002, pp. 635-700, vol. 71.
Schnare, M., et al., "Toll-Like Receptors Control Activation of Adaptive Immune Responses", "Nature Immunology", Oct. 2001, pp. 947-950, vol. 2, No. 10.
Han, J. E., et al., "Characterization of the Structure and Immunostimulatory Activity of a Vaccine Adjuvant, De-O-Acylated Lipooligosaccharide", "PLOS ONE", Jan. 2014, pp. e85838: 1-13, vol. 9, No. 1.
Arenas, J., "The Role of Bacterial Lipopolysaccharides as Immune Modulator in Vaccine and Drug Development", "Endocrine, Metabolic & Immune Disorders—Drug Targets", Jan. 1, 2012, pp. 221-235, vol. 12.
Cross, A.S., et al., "Phase I Study of Detoxified *Escherichia coli* J5 Lipopolysaccharide (J5dLPS)/group B Meningococcal Outer Membrane Protein (OMP) Complex Vaccine in Human Subjects", "Vaccine", 2003, pp. 4576-4587, vol. 21.

\* cited by examiner

FIG. 15

IMMUNE MODULATOR AND VACCINE COMPOSITION CONTAINING THE SAME

CROSS-REFERENCE TO RELATED APPLICATIONS

This application is a U.S. national phase under the provisions of 35 U.S.C. § 371 of International Patent Application No. PCT/KR17/12050 filed Oct. 30, 2017, which in turn claims priority of Korean Patent Application No. 10-2016-0142703 filed Oct. 31, 2016 and the priority of Korean Patent. Application No. 10-2017-0079762 filed Jun. 23, 2017. The disclosures of such International Patent Application No. PCT/KR17/12050, Korean Patent Application No. 10-2016-0142703, and Korean Patent Application. No. 10-2017-0079762 are hereby incorporated herein by reference in their respective entireties, for all purposes.

TECHNICAL FIELD

The present invention relates to an immune modulator having a novel structure and a vaccine composition comprising the same. More particularly, the present invention relates to an immune modulator having a novel structure, namely an analogue of lipopolysaccharide (LPS) having reduced toxicity, and uses thereof.

BACKGROUND ART

Lipopolysaccharide (LPS) is a major component of the outer membrane of gram-negative bacteria, and promotes a variety of immune cells, particularly the innate immune response. LPS activates antigen-presenting cells through the secretion of cytokines, the expression of costimulatory molecules, and the induction of antigen presentation, and links innate immune response to adaptive immune response (Akira S, Uematsu S, Takeuchi O, Cell 124: 783-801(2006); Schnare M, Barton G M, Holt A C, Takeda K, Akira S, et al. Nat Immunol 2: 947-950(2001)).

LPS consists of three domains, i.e., an amphiphilic domain (lipid A), a core oligosaccharide (OS), and an O-antigen (or O-antigenic) polysaccharide. Lipid A is known to play a role in the endotoxin activity of LPS and to exhibit immunostimulatory effects through TLR4 (toll-like receptor 4) signaling of various types of immune cells (Raetz C R, Whitfield C, Annu Rev Biochem 71: 635-700 (2002)). Lipid A derivatives, which exhibit reduced toxicity, have been targeted for the development of human vaccine immune adjuvants. Monophosphoryl lipid A (MPL) is a non-toxic derivative of LPS isolated from the *Salmonella minnesota* rough strain. In addition, a combination of an aluminum salt with MPL has been approved as an immune adjuvant for vaccines against HBV (hepatitis B virus) and HPV (human papillomavirus).

LPS has been known to have an anticancer effect since the 1950s, but has been unsuitable for use due to toxicity capable of causing death from sepsis even with contamination at the nanogram (ng) level. Thus, studies have been steadily made to reduce the toxicity of LPS and the toxicity of LPS has been successfully reduced, particularly through removal of polysaccharide chains or deacylation of lipid A (Katz S S et al., J Biol Chem. December 17; 274(51):36579-84 1999). In particular, the MPL obtained through phosphorylation of lipid A, obtained by removing the polysaccharide chain of LPS, has been developed as an immune anticancer agent free of LPS toxicity, but the effects thereof are known to be insufficient.

The present applicant has already developed a novel LPS analogue which overcomes the disadvantages of the above-mentioned immune adjuvants (Korean Patent No. 10-1509456). Numerous papers and patent documents are referenced and cited throughout the present specification. The disclosures of the cited papers and patent documents are incorporated herein by reference in their entirety to more clearly describe the state of the art to which the present invention pertains and the content of the present invention.

As a result of efforts to develop an LPS analogue capable of exhibiting excellent immunostimulatory activity while reducing toxicity, which has been a problem caused by the use of conventional LPS, the present inventors identified an EG-immune modulator (EG-IM) having a novel structure with reduced toxicity by isolating and purifying LOS not having an O-antigen site from an *E. coli* strain found in a human intestine, and deacylating the same, and found that the EG-IM can be used as an immune adjuvant due to the excellent immunostimulatory activity thereof. The present inventors have completed the present invention based on the finding that a vaccine composition comprising the immune modulator and an aluminum salt, that is, alum, exhibits immunostimulatory activity superior to the case where either the immune modulator or the aluminum salt is used alone.

DISCLOSURE

Technical Problem

Therefore, it is one object of the present invention to provide an immune modulator represented by the following Formula 1 with a novel structure and an immune adjuvant composition comprising the immune modulator as an active ingredient:

[Formula 1]

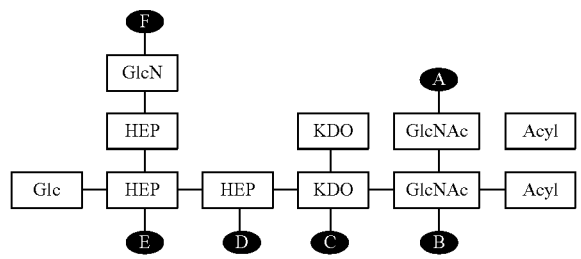

wherein Glc is glucose, GlcN is glucosamine, HEP is heptose, KDO is 2-keto-3-deoxy-octonate, GlcNAc is N-acetylglucosamine, and A to F are positions to which phosphate can be bonded.

It is another object of the present invention to provide a vaccine composition comprising: (a) an antigen; (b) the immune modulator represented by Formula 1; and (c) alum.

Technical Solution

To achieve the above object, the present invention provides an immune modulator represented by the following Formula 1:

[Formula 1]

wherein Glc is glucose, GlcN is glucosamine, HEP is heptose, KDO is 2-keto-3-deoxy-octonate, GlcNAc is N-acetylglucosamine, and A to F are positions to which phosphate can be bonded.

The present invention also provides an immune adjuvant composition comprising the immune modulator as an active ingredient.

The present invention also provides a vaccine composition comprising: (a) an antigen; (b) the immune modulator represented by Formula 1; and (c) alum.

The present invention also provides a method for preventing an immune disease including treating a patient with the immune modulator represented by Formula 1 and a use of the immune modulator for the prevention of an immune disease.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3 shows the results of analysis of IL-6, IL-12p40 and TNF-α, FIG. 4 shows the results of analysis of IL-5 and IL-10, and FIG. 5 shows the results of analysis of MCP-1 and RANTES.

FIGS. 14 and 15 show the results of measurement of a *P. aeruginosa* antigen-specific antibody titer when using a combination of EG-IM/alum. FIG. 14 shows immunization with a *P. aeruginosa* FT2 antigen, and FIG. 15 shows immunization with a *P. aeruginosa* FT1 antigen.

DETAILED DESCRIPTION OF THE INVENTION

Figure 1:
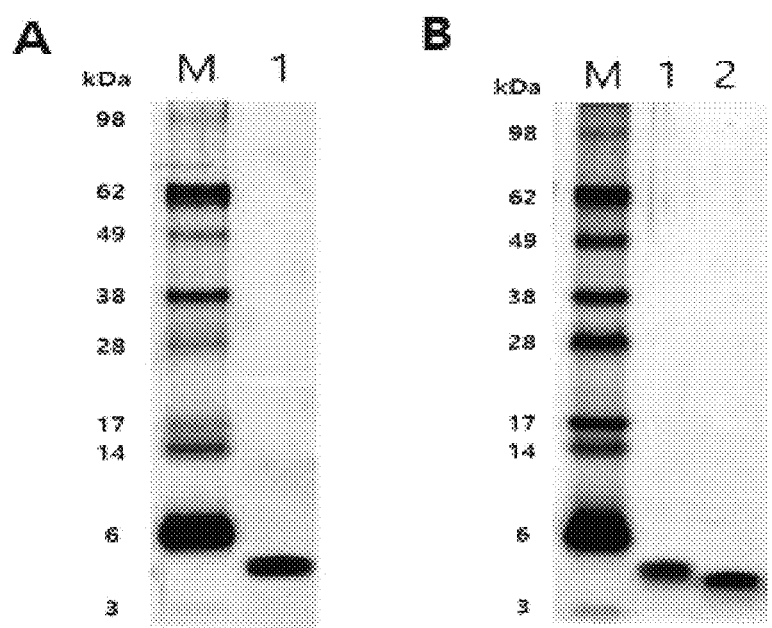
FIG. 1 in image A shows the results of identification of the extracted LOS through electrophoresis and silver staining, and in image B shows a result indicating that the size of EG-IM decreases, based on LOS extracted by O-acyl chain removed lipid A when treating LOS with an alkali, wherein M represents a marker, lane 1 represents LOS extracted before deacylation, and lane 2 represents an immune modulator (EG-IM).

Unless defined otherwise, all technical and scientific terms used herein have the same meanings as appreciated by those skilled in the field to which the present invention pertains. In general, the nomenclature used herein and the experimentation method described below are well-known in the art and are ordinarily used.

In one embodiment of the present invention, an EG-immune modulator (EG-IM) was obtained by preparing dried bacteria cells using *E. coli*, extracting LOS and then removing the toxicity of LOS using alkali treatment, and MS analysis identified that the immune modulator (EG-IM) has the structure of Formula 1.

Accordingly, in one aspect, the present invention is directed to an immune modulator represented by the following Formula 1:

[Formula 1]

wherein Glc is glucose, GlcN is glucosamine, HEP is heptose, KDO is 2-keto-3-deoxy-octonate, GlcNAc is N-acetylglucosamine, and A to F are positions to which phosphate can be bonded.

As used herein, the term "LOS (lipooligosaccharide)" refers to a variant of LPS (lipopolysaccharide) that has a shorter sugar chain than natural LPS and thus has a lower molecular weight. LOS prior to deacylation preferably has a molecular weight of 3,000 to 10,000 Da, more preferably 3,000 to 4,000 Da. The term "deacylated LOS" refers to LOS in which the fatty acid linked to the glucosamine of lipid A via a —C(O)O— bond is removed therefrom and the toxicity is greatly reduced compared to LOS. The fatty acid is linked to lipid A glucosamine via —C(O)O— and —C(O)NH— bonds. The deacylated LOS of the present invention is LOS from which the fatty acid linked via the —C(O)O— bond is removed through deacylation of lipid A.

The EG-IM can be prepared by various methods, but can be prepared in accordance with the methods disclosed in the preceding patents of the present inventors, namely Korean Patent No. 0456681; WO 2004/039413; Korean Patent No. 0740237; and WO 2006/121232. For example, LPS is deacylated by treatment with a strong base (e.g., 0.2 N NaOH) to remove some fatty acids from lipid A to thereby detoxify the same.

According to the present invention, the EG-IM can be linked to 2 to 6 phosphate groups, preferably 3 to 4 phosphate groups, but not limited thereto. In addition, the number and positions of the phosphate groups in Formula 1 may be the same as those exemplified in Table 1 below.

TABLE 1

| Item | Number of phosphate groups | Positions of phosphate groups |
| --- | --- | --- |
| Example 1 | 2 | A, B |
| Example 2 | 2 | A, C |
| Example 3 | 2 | A, D |
| Example 4 | 2 | A, E |
| Example 5 | 2 | A, F |
| Example 6 | 2 | B, C |
| Example 7 | 2 | B, D |
| Example 8 | 2 | B, E |
| Example 9 | 2 | B, F |
| Example 10 | 2 | C, D |
| Example 11 | 2 | C, E |
| Example 12 | 2 | C, F |
| Example 13 | 2 | D, E |
| Example 14 | 2 | D, [[E]] F |
| Example 15 | 2 | E, F |
| Example 16 | 3 | A, B, C |
| Example 17 | 3 | A, B, D |
| Example 18 | 3 | A, B, E |
| Example 19 | 3 | A, B, F |
| Example 20 | 3 | A, C, D |
| Example 21 | 3 | A, C, E |
| Example 22 | 3 | A, C, F |

TABLE 1-continued

| Item | Number of phosphate groups | Positions of phosphate groups |
| --- | --- | --- |
| Example 23 | 3 | A, D, E |
| Example 24 | 3 | A, D, F |
| Example 25 | 3 | A, E, F |
| Example 26 | 3 | B, C, D |
| Example 27 | 3 | B, C, E |
| Example 28 | 3 | B, C, F |
| Example 29 | 3 | B, D, E |
| Example 30 | 4 | B, D, F |
| Example 31 | 3 | B, E, F |
| Example 32 | 3 | C, D, E |
| Example 33 | 3 | C, D, F |
| Example 34 | 3 | C, E, F |
| Example 35 | 3 | D, E, F |
| Example 36 | 4 | A, B, C, D |
| Example 37 | 4 | A, B, C, E |
| Example 38 | 4 | A, B, C, F |
| Example 39 | 4 | A, B, D, E |
| Example 40 | 4 | A, B, D, F |
| Example 41 | 4 | A, B, E, F |
| Example 42 | 4 | A, C, D, F |
| Example 43 | 4 | A, C, D, F |
| Example 44 | 4 | A, D, E, F |
| Example 45 | 5 | A, B, C, D, E |
| Example 46 | 5 | A, B, C, D, F |
| Example 47 | 6 | A, B, C, D, E, F |

The phosphate is bonded at a position selected from the group consisting of AB, AC, AD, AE, AF, BC, BD, BE, BF, CD, CE, CF, DE, DF, EF, ABC, ABD, ABE, ABF, ACD, ACE, ACF, ADE, ADF, AEF, BCD, BCE, BCF, BDE, BDF, BEF, CDE, CDF, CEF, DEF, ABCD, ABCE, ABCF, ABDE, ABDF, ABEF, ACDE, ACDF, ADEF, BCDE, BCDF, BCEF, BDEF, CDEF, ABCDE, ABCEF and ABCDEF of Formula 1.

According to the present invention, the sugar in Formula 1 is selected from the group consisting of hexose, hexosamine, N-acetylhexosamine, heptose and Kdo (2-keto-3-deoxy-octonate).

As used herein, the term "hexose" means a monosaccharide including six carbon atoms in a molecule, and examples thereof include, but are not limited to, ketohexose (psicose, fructose, sorbose, tagatose), aldohexose (allose, altrose, glucose, mannose, gulose, idose, galactose, talose) and deoxy sugars (fucose, fuculose, rhamnose).

According to the present invention, the hexose is aldohexose, and in a specific example, the aldohexose is glucose or galactose.

As used herein, the term "heptose" refers to a monosaccharide containing seven carbon atoms in a molecule, and may be classified into aldoheptose (position 1) and ketoheptose (position 2) depending on the position of functional groups (aldehyde and ketone groups). The aldoheptose is, for example, L-glycero-D-manno-heptose, but is not limited thereto. The ketoheptose is, for example, sedoheptulose and mannoheptulose, but is not limited thereto.

According to the present invention, the hexosamine is glucosamine, galactosamine or mannosamine, and in a specific example, the hexosamine is glucosamine.

According to the present invention, the hexosamine is glucosamine, galactosamine or mannosamine, and in a specific example, the hexosamine is glucosamine.

According to the present invention, the N-acetylhexosamine is N-acetylglucosamine, N-acetylgalactosamine or N-acetylmannosamine, and in a specific example, the N-acetylhexosamine is N-acetylglucosamine.

The EG-IM of the present invention has fewer sugars than wild-type LPS. According to one embodiment of the present invention, the EG-IM may include 5 to 7 sugars. In a specific example, the EG-IM includes 6 or 7 sugars, but is not limited thereto.

The EG-IM of the present invention does not have O-linked fatty acids.

The EG-IM of the present invention is characterized in that it has remarkably reduced toxicity because a fatty acid (for example, a C14 fatty acid) is removed (deacylated) from lipid A. The fatty acid is linked to glucosamine in lipid A via a —C(O)O— or —C(O)NH— bond. In the present invention, deacylation means removal of a fatty acid linked via a —C(O)O— bond.

The deacylation may be carried out by treating LOS with an alkali, and the alkali includes NaOH, KOH, Ba(OH)$_2$, CsOH, Sr(OH)$_2$, Ca(OH)$_2$, LiOH, RbOH, and Mg(OH)$_2$, more preferably NaOH, KOH, Ba(OH)$_2$, Ca(OH)$_2$, LiOH and Mg(OH)$_2$, even more preferably NaOH, KOH and Mg(OH)$_2$, and most preferably NaOH.

The EG-IM of the present invention is derived from *E. coli*, and the *E. coli* is *Escherichia coli* EG0024 (Accession No.: KCTC 12948BP). The strain was deposited on Nov. 19, 2015 with the deposit number KCTC 12948BP in the Korean Collection for Type Cultures of the Korea Research Institute of Bioscience and Biotechnology.

According to the present invention, the EG-IM exhibits immunostimulatory activity.

As used herein, the term "immunostimulation" refers to inducing an initial immune response or increasing a conventional immune response to an antigen to a measurable extent.

In another embodiment of the present invention, EG-IM is administered to mice to analyze the level of mouse serum cytokine. As a result, it is found that the EG-IM induces the secretion of cytokines such as TNF-α, IL-5, IL-6, IL-10, IL-12p40, MCP-1, and RANTES.

Thus, in another aspect, the present invention is directed to an immune adjuvant composition comprising the EG-IM as an active ingredient.

The EG-IM of the present invention is particularly suitable for the vaccine composition of the present invention because it exhibits excellent immunostimulatory effects and reduced toxicity, as compared to conventional immune adjuvants. The EG-IM of the present invention is less toxic than MPL (monophosphoryl lipid A), obtained through phosphorylation of lipid A, obtained by removing the polysaccharide chain of LPS in order to remove the toxicity of LPS.

The immune adjuvant composition of the present invention can induce a sufficient immune response even with the EG-IM alone and thus exert preventive effects against various diseases. Specifically, the immune adjuvant composition can be used for the treatment of cancer or immune diseases.

According to the present invention, the cancer may be fibrosarcoma, bladder cancer, pituitary adenoma, glioma, brain tumor, nasopharyngeal cancer, laryngeal cancer, thymoma, mesothelioma, breast cancer, lung cancer, gastric cancer, esophageal cancer, colon cancer, liver cancer, pancreatic cancer, pancreatic endocrine tumor, gallbladder cancer, penile cancer, ureteral cancer, renal cell carcinoma, prostate cancer, non-Hodgkin's lymphoma, myelodysplastic syndrome, multiple myeloma, plasma cell tumors, leukemia, pediatric cancer, skin cancer, ovarian cancer, or cervical cancer, but is not limited thereto.

According to the present invention, the immune disease may be atopic dermatitis, asthma, psoriasis, allergic conjunctivitis, allergic rhinitis, allergic granuloma, allergic dermatitis, gastrointestinal allergies, hypersensitivity pneumonitis, food hypersensitivities, urticaria, eczema, rheumatoid arthritis, ankylosing spondylitis, cystic fibrosis, late or chronic solid organ transplantation rejection, multiple sclerosis, systemic lupus erythematosus, Sjogren's syndrome, Hashimoto's thyroid gland, multiple myositis, scleroderma, Addison's disease, vitiligo, malignant anemia, glomerulonephritis, pulmonary fibrosis, inflammatory bowel disease, or Grave's disease, but is not limited thereto.

In addition, optionally, the immune adjuvant composition of the present invention may further contain another immune adjuvant ingredient, for example, a Group II element selected from the group consisting of Mg, Ca, Sr, Ba and Ra, or a salt thereof; a Group IV element selected from the group consisting of Ti, Zr, Hf and Rf, or an aluminum salt or hydrate thereof; or dimethyloctadecylammonium bromide. The salt is formed with, for example, an oxide, peroxide, hydroxide, carbonate, phosphate, pyrophosphate, hydrogen phosphate, dihydrogen phosphate, sulfate or silicate.

According to the present invention, the immune adjuvant ingredient that may be further contained in the immune adjuvant composition of the present invention is selected from the group consisting of magnesium hydroxide, magnesium carbonate, hydroxide pentahydrate, titanium dioxide, calcium phosphate, calcium carbonate, barium oxide, barium hydroxide, barium peroxide, barium sulfate, calcium sulfate, calcium pyrophosphate, magnesium carbonate, magnesium oxide, aluminum hydroxide, aluminum phosphate and hydrated aluminum potassium sulfate.

According to the present invention, the immune adjuvant composition may further contain aluminum hydroxide or calcium phosphate.

In another embodiment of the present invention, vaccines are prepared by mixing an EG-IM and alum with a Japanese encephalitis virus (JEV) antigen, a *Haemophilus* b (HIB) antigen, a recombinant MERS-CoV S1 protein, a recombinant MERS-CoV S1 RBD protein, a Zika virus envelope protein, and a *Pseudomonas aeruginosa* FT2 antigen or FT1 antigen in order to identify the immunogenicity enhancement effect of EG-IM and alum. Each vaccine is administered to mice, titers are measured, and cytokines are analyzed. As a result, it was found that each of the vaccines has excellent antibody-mediated immune efficacy and/or cellular immune efficacy.

In another aspect, the present invention is directed to a vaccine composition comprising: (a) an antigen; (b) the immune modulator represented by Formula 1; and (c) alum.

In another aspect, the present invention is directed to a method for preventing an immune disease, including administering the immune modulator represented by Formula 1 to a patient in need of treatment, or a use of the immune modulator for the prevention of an immune disease.

As used herein, the term "antigen" refers to a substance that induces an immune response. Therefore, in the present invention, any substance exhibiting such activity of inducing an immune response can be used without limitation.

The antigen of the present invention may be a peptide, a protein, a nucleic acid, a sugar, a pathogen, an attenuated pathogen, an inactivated pathogen, a virus, a virus-like particle (VLP), a cell or a cell fragment.

In the present invention, the antigen is selected from the group consisting of an antigen of Japanese encephalitis virus, an antigen of *Haemophilus influenzae* type B (HIB), an antigen of Middle East Respiratory Syndrome (MERS) virus, an antigen of Zika virus, an antigen of *Pseudomonas aeruginosa*, an antigen of pertussis, an antigen of *Mycobacterium tuberculosis*, an antigen of anthrax, an antigen of hepatitis A virus (HAV), an antigen of hepatitis B virus (HBV), an antigen of hepatitis C virus (HCV), an antigen of human immunodeficiency virus (HIV), an antigen of herpes simplex virus (HSV), an antigen of *Neisseria meningitidis*, an antigen of *Corynebacterium diphtheria*, an antigen of *Bordetella pertussis*, an antigen of *Clostridium tetani*, an antigen of human papilloma virus (HPV), an antigen of Varicella virus, an antigen of Enterococci, an antigen of *Staphylococcus aureus*, an antigen of *Klebsiella pneumoniae*, an antigen of *Acinetobacter baumannii*, an antigen of *Enterobacter*, an antigen of *Helicobacter pylori*, an antigen of malaria, an antigen of a dengue virus, an antigen of *Orientia tsutsugamushi*, an antigen of severe fever with thrombocytopenia syndrome Bunyavirus (SFTS Bunyavirus), an antigen of severe acute respiratory syndrome-coronavirus (SARS-CoV), an antigen of an influenza virus, an antigen of an Ebola virus and an antigen of *Diplococcus pneumoniae*.

The vaccine composition of the present invention can induce a sufficient immune response and thus exert preventive efficacy against a specific disease, even with a basic composition thereof, that is, an antigen and an EG immune modulator (EG-IM) alone. Optionally, the vaccine composition of the present invention may further contain the additional immune adjuvant ingredient described above.

In addition, according to the present invention, the vaccine may be in the form of an inactivated vaccine, an attenuated vaccine, a subunit vaccine, a recombinant vaccine, a protein-conjugated vaccine, a monovalent vaccine, a multivalent vaccine, or a mixed vaccine.

The vaccine according to the present invention can be a Japanese encephalitis vaccine, a *Haemophilus influenzae* type B vaccine, a MERS vaccine, a Zika vaccine, a *Pseudomonas aeruginosa* vaccine, a cancer vaccine, a tuberculosis vaccine, an anthrax vaccine, an HAV vaccine, an HBV vaccine, an HCV vaccine, an HIV vaccine, a herpes simplex vaccine, a meningococcal vaccine, a diphtheria vaccine, a pertussis vaccine, a tetanus vaccine, a varicella vaccine, a multidrug-resistant bacteria vaccine, an Enterococci vaccine, a *Staphylococcus aureus* vaccine, a *Klebsiella pneumoniae* vaccine, an *Acinetobacter baumannii* vaccine, an *Enterobacter* vaccine, a *Helicobacter pylori* vaccine, a malaria vaccine, a dengue virus vaccine, an *Orientia tsutsugamushi* vaccine, a severe fever with thrombocytopenia syndrome Bunyavirus (SFTS bunyavirus) vaccine, a severe acute respiratory syndrome-coronavirus (SARS-CoV) vaccine, an influenza virus vaccine, an Ebola virus vaccine or a *Diplococcus Pneumoniae* vaccine, preferably a Japanese encephalitis vaccine, a *Haemophilus influenzae* type B vaccine, a MERS vaccine, a Zika vaccine, or a *Pseudomonas aeruginosa* vaccine.

The cancer vaccine may be selected from the group consisting of vaccines of fibrosarcoma, bladder cancer, pituitary adenoma, glioma, brain tumors, nasopharyngeal cancer, laryngeal cancer, thymoma, mesothelioma, breast cancer, lung cancer, gastric cancer, esophageal cancer, colon cancer, liver cancer, pancreatic cancer, pancreatic endocrine tumor, gallbladder cancer, penile cancer, ureteral cancer, renal cell carcinoma, prostate cancer, non-Hodgkin's lymphoma, myelodysplastic syndrome, multiple myeloma, plasma cell tumor, leukemia, pediatric cancer, skin cancer, ovarian cancer, and cervical cancer, but is not limited thereto.

The vaccine according to the present invention may contain 1 to 10% by weight of the immune modulator based on the total weight of the composition. When the immune modulator is contained in an amount less than 1% by weight, an effective immune effect cannot be expected. When the immune modulator is contained in an amount exceeding 30% by weight, immune tolerance may occur.

The vaccine according to the present invention may contain 70 to 99% by weight of the alum based on the total weight of the composition. When the immune modulator is contained in an amount of less than 70% by weight, an effective immune effect cannot be expected.

The vaccine composition of the present invention may contain a pharmaceutically acceptable carrier and contain an ingredient generally used for formulation, such as lactose, dextrose, sucrose, sorbitol, mannitol, starch, acacia gum, calcium phosphate, alginate, gelatin, calcium silicate, microcrystalline cellulose, polyvinyl pyrrolidone, cellulose, water, syrup, methyl cellulose, methylhydroxy benzoate, propyl hydroxybenzoate, talc, magnesium stearate and mineral oil, but is not limited thereto. The vaccine composition of the present invention may further contain a lubricant, a wetting agent, a sweetener, a flavor, an emulsifier, a suspending agent, a preservative or the like, in addition to the ingredients described above. Suitable pharmaceutically acceptable carriers and formulations are described in detail in Remington's Pharmaceutical Sciences (19th ed., 1995).

The vaccine composition of the present invention can be administered orally or parenterally. In the case of parenteral administration, the vaccine composition can be administered through intravenous injection, subcutaneous injection, muscular injection, intraperitoneal injection, transdermal administration or the like.

A suitable dosage of the vaccine composition of the present invention may be variably prescribed based on factors such as the formulation method, administration method, and age, body weight, gender, pathological condition, food, administration time, administration route, excretion rate and responsiveness of a patient.

The vaccine composition of the present invention may be prepared in a single-dose form or may be embedded into a multi-dose vial by formulating using a pharmaceutically acceptable carrier and/or excipient according to a method that can be easily implemented by a person having ordinary skill in the art to which the present invention pertains. At this time, the formulation may be in the form of a solution, suspension or emulsion in an oil or aqueous medium, or in the form of an extract, powder, granule, tablet or capsule, and may additionally contain a dispersant or a stabilizer.

Hereinafter, the present invention will be described in more detail with reference to the following examples. However, it will be obvious to those skilled in the art that these examples are provided only for illustration of the present invention and should not be construed as limiting the scope of the present invention.

Preparation Example: Preparation of Immune Modulator (EG-IM)

1. Preparation of Dried Strain Cell

E. coli was cultured with shaking at 80 rpm or less in 30 g/l of a TSB (Tryptic soy broth, Difco) medium at 37° C. for 20 hours, and the cells were collected using a centrifuge. The collected cells were mixed with ethanol and centrifuged to obtain a precipitate. Then, acetone was added to the obtained precipitate, thoroughly mixed and then centrifuged to obtain a precipitate. Ethyl ether was added to the obtained precipitate, thoroughly mixed and then centrifuged to obtain a precipitate. The obtained precipitate was dried in a drying oven at 60° C. to prepare dried bacteria cells.

2. LOS Extraction

After measuring the weight of the dried bacteria cells, 7.5 mL of a PCP (phenol, chloroform, petroleum ether) extract solution was added per 1 g of the weight to separate LOS from the bacteria cells. The organic solvent was removed at a high temperature from the LOS extract obtained by the method using a rotary evaporator. The remaining extract was centrifuged at a high temperature to obtain a precipitate, and the precipitate was washed with ethyl ether. Purified water was then added thereto to form a precipitate. The formed precipitate was centrifuged and separated from the supernatant, and the remaining precipitate was washed with ethanol and thus collected. The precipitate was thoroughly dried in a high-temperature drying oven and the precipitate was dissolved in purified water to extract LOS.

3. Removal of LOS Toxicity

After determining the content of the LOS extract, the concentration of the LOS extract was adjusted to 3 mg/mL and the LOS extract was mixed with 0.2N NaOH at a volume ratio of 1:1. The reaction was allowed to proceed in a constant-temperature water bath at 60° C. for 120 minutes and stirred using a vortex for 5 seconds every 10 minutes. Then, 1N acetic acid was added thereto in an amount of about ⅕ of the initial amount of 0.2N NaOH. Then, EG-IM, an immune modulator, was obtained through ethanol precipitation.

4. Quantification and Identification of LOS and EG-IM

The contents of LOS and EG-IM were measured by KDO (2-keto-3-dioxyoctonate) assay using 2-thiobarbituric acid, the concentrations thereof were measured, and LOS and EG-IM were separated based on size through SDS-PAGE and identified by silver staining, and are shown in FIG. 1. FIG. 1 in image A shows the results of identification of the extracted LOS through electrophoresis and silver staining. FIG. 1 in image B shows a result indicating that the size of EG-IM decreases based on LOS extracted by degradation of lipid A when treating LOS with an alkali, wherein M represents a marker (SeeBlue® Plus 2 prestained standard, Invitrogen, LC5952), lane 1 represents LOS extracted before deacylation, and lane 2 represents EG-IM, deacylated LOS.

Example 1: Structural Analysis of Immune Modulator (EG-IM)

Figure 2:
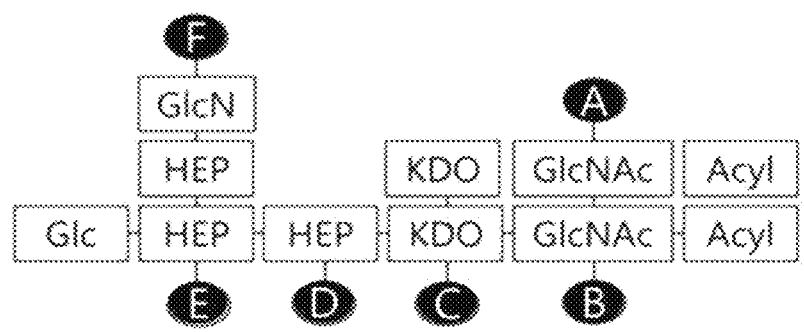
FIG. 2 shows the structure of the EG-immune modulator (EG-IM) according to the present invention, wherein Glc is glucose, GlcN is glucosamine, HEP is heptose, KDO is 2-keto-3-deoxy-octonate, GlcNAc is N-acetylglucosamine, and A to F are positions to which phosphates can be bonded.

The purified sample was suitably diluted with purified water. A CU18 reverse-phase column (ACQUITY BEH300 C18 1.7 um 2.1×150 mm) was mounted on the instrument (UPLC, Water) and the sample was then separated at a concentration gradient of 35 to 95% using mobile phase A (50 mM ammonium formate pH 4.5) and mobile phase B (100% acetonitrile). MS analysis and MS/MS analysis were conducted with a mass spectrometer (VELOS PRO, Thermo). Molecules having a molecular weight of 100 to 3,000 m/z were analyzed. After MS analysis, the identified molecules having a molecular weight of 50 to 2,000 m/z were analyzed once again. A molecule having a molecular weight of 2,372 m/z was identified as a major ingredient, and a structural schematic diagram obtained by analyzing each peak is shown in FIG. 2.

Example 2: Immune Response Analysis of Immune Modulator (EG-IM)

1. Immunization and Blood Sampling

3 μg of EG-IM or MPL according to the present invention was administered to the deltoid of the femoral region of the hindlimb of 6-week-old mice (BALB/c, female, central laboratory animal/SLC Japan) which came in at 5-week-old and rarefied for one week (n=3). Saline was administered to mice of a control group. One and four hours after administration, a rompun/ketamine anesthetic solution was intraperitoneally administered to anesthetize the mice and blood was collected from the heart. The blood was allowed to stand under a refrigeration condition for about 4 hours, and the serum was separated by centrifugation at 4° C. and 3,000 rpm for 10 minutes, transferred to a new tube and stored at −70° C.

2. Analysis of Levels of Cytokine in Mouse Serum

Figure 3:
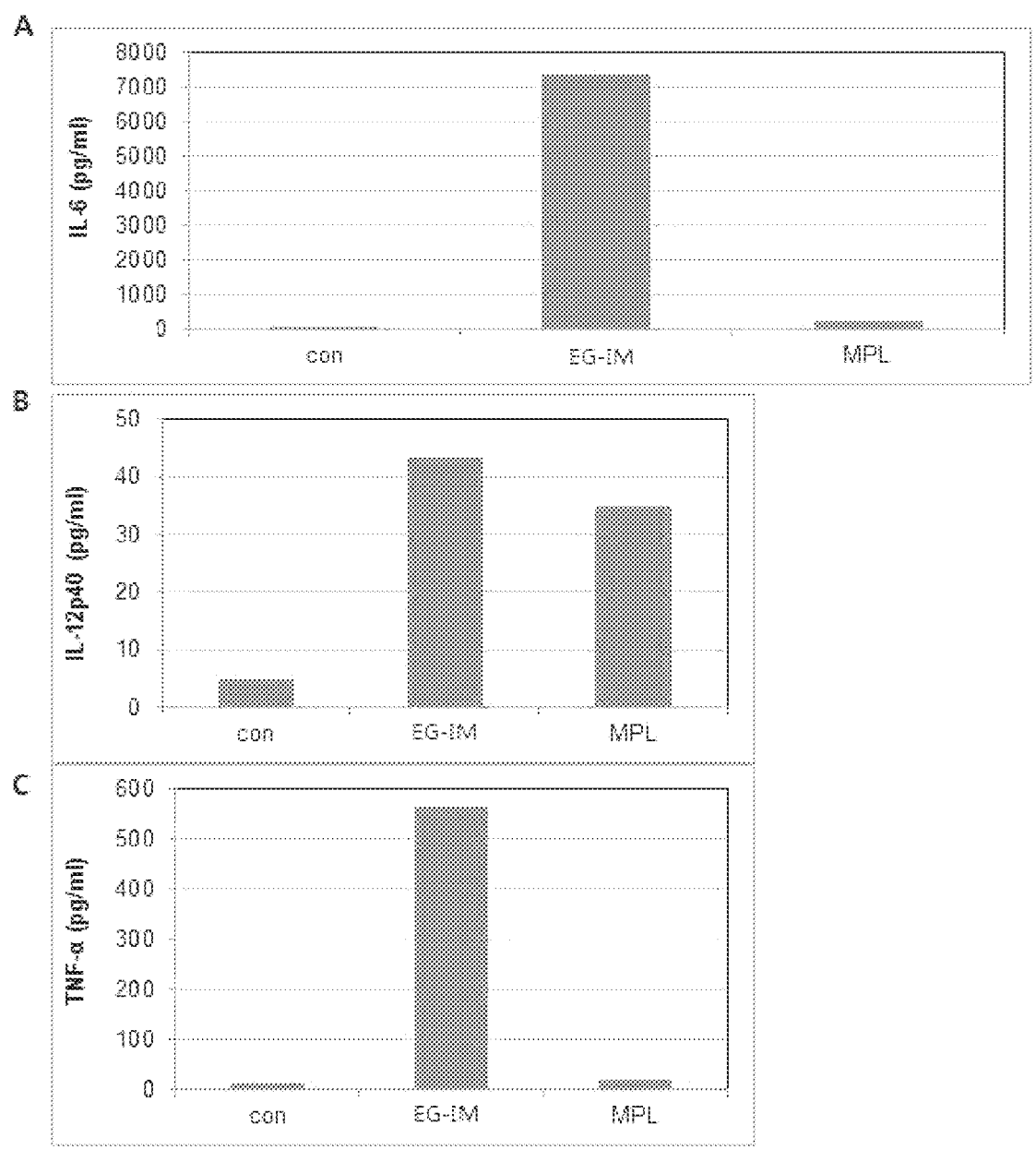
FIGS. 3 to 5 show results of analysis of cytokine levels in sera. 1 and 4 hours after administration of 3 μg of an immune modulator (EG-IM) or MPL, cardiac blood collected from mice (n=3) was analyzed.
Figure 4:
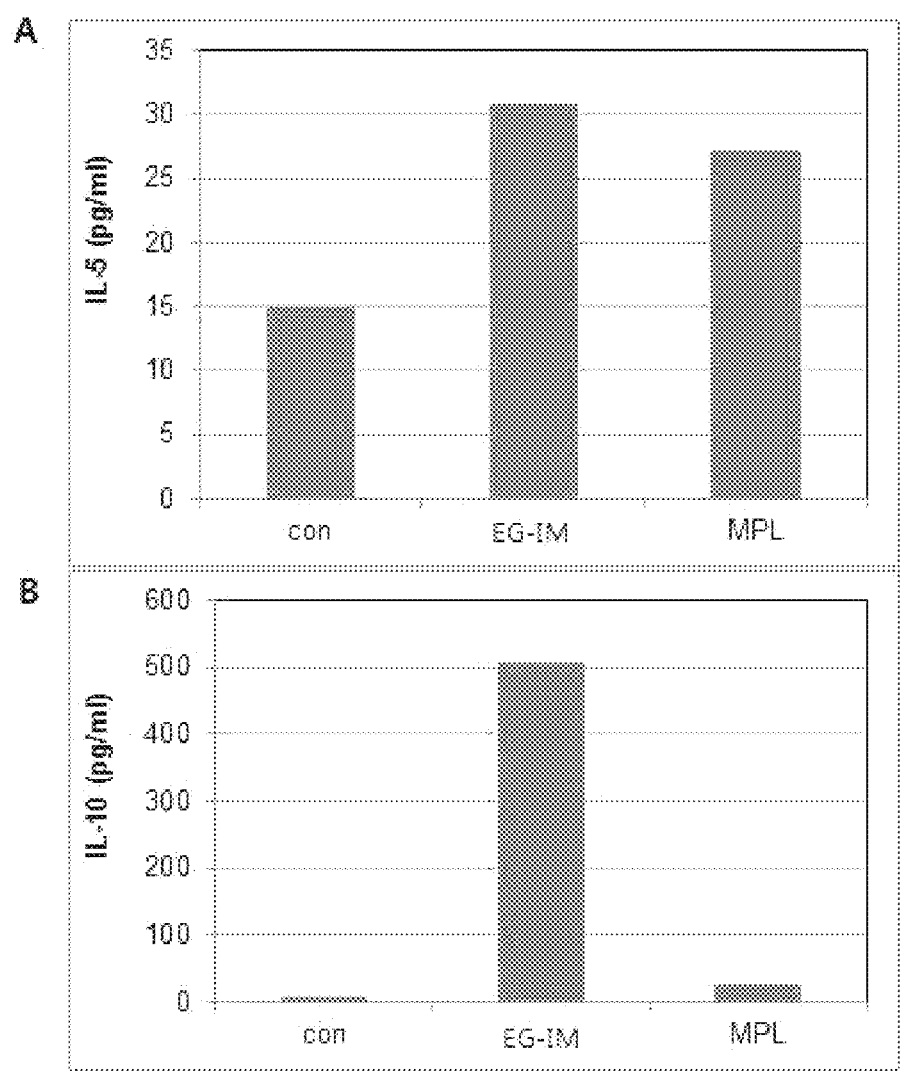
Figure 5:
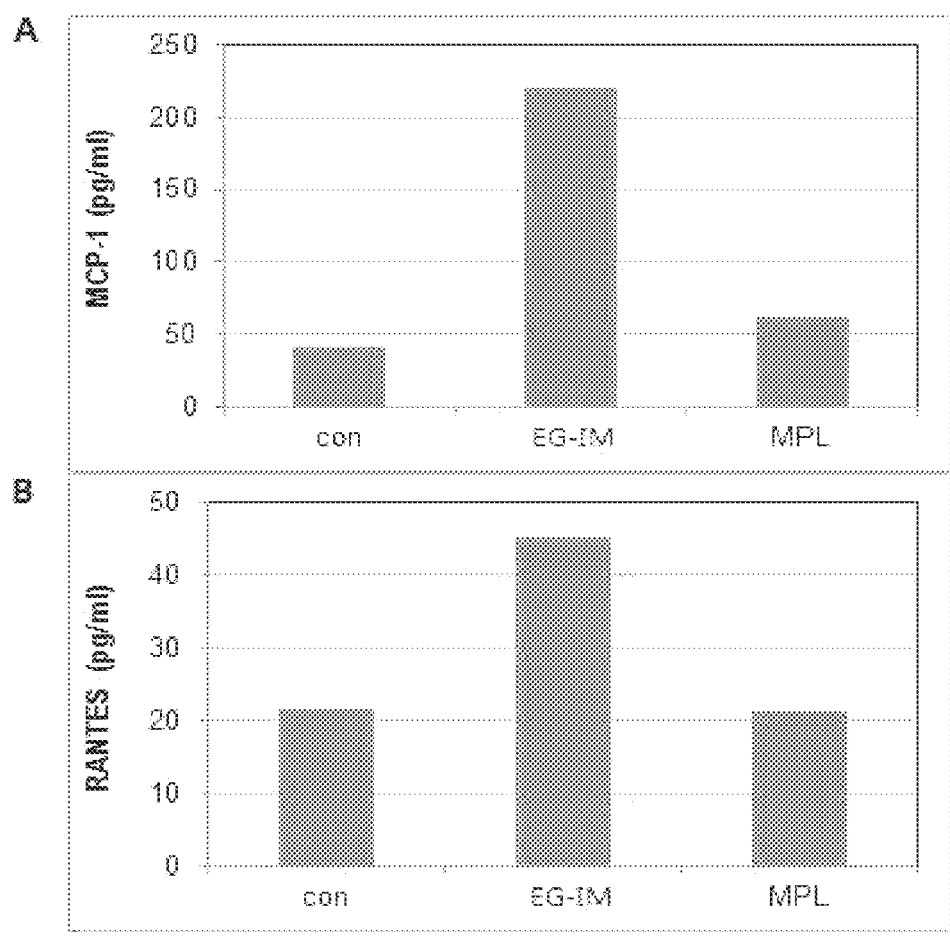

Multiplex cytokine assay (Millipore MAP assay kit, Millipore, Billerica, Mass., USA) was performed to measure levels of cytokines and chemokines. The target cytokines were TNF-α, IL-5, IL-6, IL-10, IL-12p40, MCP-1, and RANTES, and test results were analyzed using an assay instrument [Luminex 200 (Millipore)] and an assay program [MILLIPLEX Analyst (Millipore)] and are shown in FIGS. 3 to 5. FIG. 3 shows the results of analysis of IL-6, IL-12p40 and TNF-α, FIG. 4 shows the results of analysis of IL-5 and IL-10, and FIG. 5 shows the results of analysis of MCP-1 and RANTES.

As can be seen from FIGS. 3 to 5, when EG-IM is administered, it induces secretion of TNF-α and IL-6 as inflammation-inducing cytokines, IL-12p40 as Th1-type cytokine, and IP-10, MIG-1, MCP-1 and RANTES as chemokines. In addition, the level of the immune modulator-inducing cytokine was higher than that induced by MPL. This means that in vivo immunostimulatory activity of EG-IM, an immune modulator, is superior to MPL.

Example 3: Analysis of Efficacy of EG-IM/Alum in Inactivated Vaccine

1. Immunization of Japanese Encephalitis Vaccine

A Japanese encephalitis virus (JEV) antigen was used in order to identify the immunogenicity enhancement effect of EG-IM/Alum in inactivated vaccine. An inactivated Japanese encephalitis vaccine, or a combination of a Japanese encephalitis vaccine and alum (aluminum hydroxide; Brenntag, Germany) was administered to 6-week old BALB/c mice (Koatec, Korea) twice at intervals of two weeks. The combination was prepared such that the inactivated Japanese encephalitis vaccine was used in an amount of 0.5 μg/mouse or 1 μg/mouse, alum was used in an amount of 25 μg/mouse and EG-IM was used in an amount of 0.5 μg/mouse to yield a final volume of 100 μl. The negative control group was administered PBS (phosphate-buffered saline, pH 7.3).

2. Measurement of JEV Antigen-Specific Antibody Titers

Figure 6:
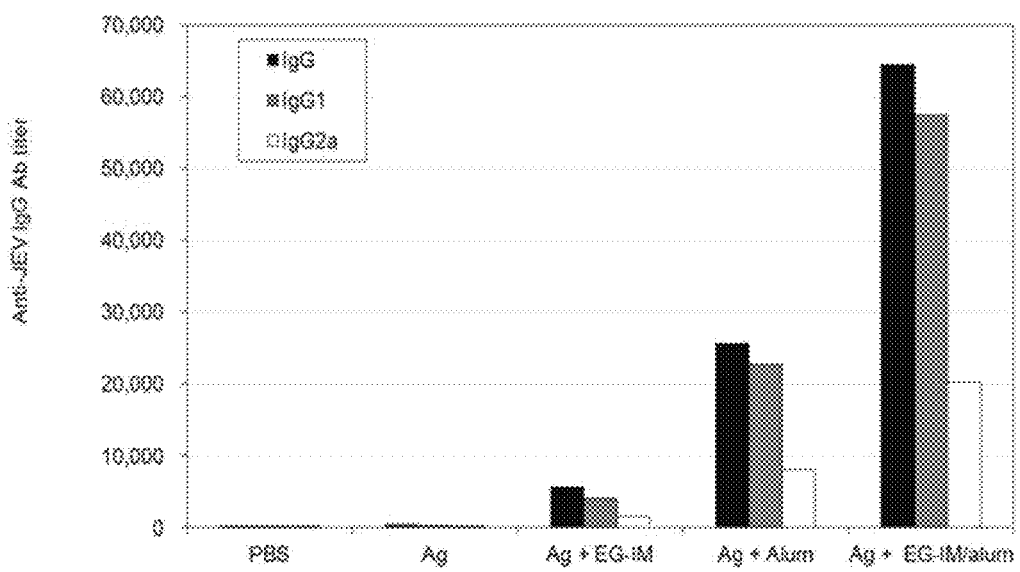
FIG. 6 shows the results of measurement of Japanese encephalitis virus (JEV) antigen-specific antibody titers when using a combination of EG-IM/alum.

Two weeks after the last administration, mice were anesthetized and cardiac blood was collected therefrom to prepare a blood sample. An end-point dilution enzyme-linked immunosorbent assay method was used in order to measure the titer of an antibody specific to a JEV antigen in serum after immunization. JEV was diluted to a concentration of 1 μg/ml, coated on a 96-well plate at 100 μl/well (overnight at 4° C.) and blocked with 300 μl of 1% BSA (bovine serum albumin) (room temperature, 1 hour). After blocking, washing three times with PBS containing 0.05% Tween-20, and the serum obtained after immunization was diluted by 10-fold serial dilution and 100 μl of each diluted serum was reacted (37° C., 2 hours). In order to identify the JEV antigen-specific antibody, a horseradish peroxidase-conjugated anti-mouse IgG antibody (Jackson, 115-035-003), an IgG1 antibody (Serotec, STAR132P), and an IgG2a antibody (Serotec, STAR133P) were allowed to react, then TMB (tetramethylbenzidine, BD Bio science, 55555214) was added thereto, and the reaction was stopped with 1N $H_2SO_4$. Test results were obtained by measuring absorbance at 450 nm and measuring titers of IgG, IgG1 and IgG2a antibodies in blood collected after immunization. As a result, in the test group using EG-IM/alum, production of JEV virus antigen-specific IgG antibody was increased by 13-fold and 3-fold, respectively, as compared to the test group using EG-IM alone or alum alone. In addition, the production of the JEV virus antigen-specific IgG1 antibody of the test group using EG-IM/alum was increased by 12-fold and 3-fold, respectively, as compared to the test group using EG-IM alone or alum alone, and the production of the JEV virus antigen-specific IgG2a antibody was also increased in the test group using EG-IM/Alum (FIG. 6).

Thus, the Japanese encephalitis vaccine of the present invention containing EG-IM as an immune modulator as well as alum as an immune adjuvant shows excellent immunity, that is, vaccine efficacy.

3. Cytokine Analysis

Two weeks after the final administration, mice were anesthetized, and spleen tissues were extracted and separated into single cells, stimulated with 5 μg/ml of an inactivated JEV antigen or a recombinant JEV gE protein, and cultured for 72 hours. Then, secretion of IFN-γ and IL-5 cytokines was analyzed by sandwich ELISA (R&D systems, DY485; DY405).

Figure 7:
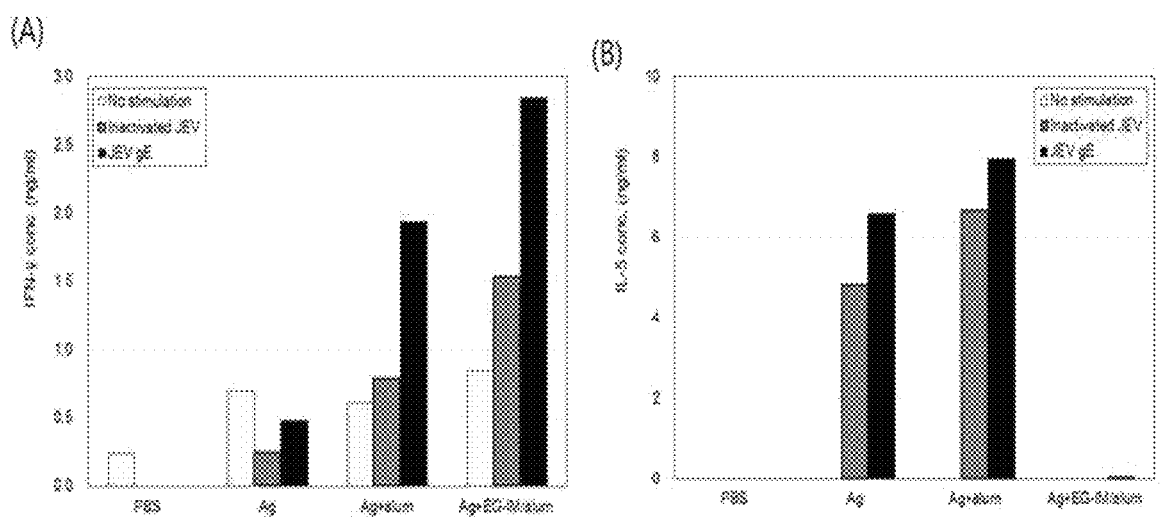
FIG. 7 shows the results of measurement of secretion levels of IFN-γ and IL-5 cytokines when administering a Japanese encephalitis vaccine.

As a result, the test group using EG-IM/alum enhanced IFN-γ secretion, as compared to the test group using alum alone which functions to improve humoral immunity, but did not enhance IL-5 secretion (FIG. 7).

Thus, it can be found that the Japanese encephalitis virus vaccine containing EG-IM and alum has excellent ability to induce TH1-type cellular immunity as well as antibody-mediated immune response.

Example 4: Analysis of Efficacy of EG-IM/Alum in Conjugate Vaccine

1. Immunization of B-Type *Haemophilus influenza* Vaccine

An HIB (haemophilus b) antigen was used to identify the immunogenicity enhancement effect of EG-IM/alum in the conjugate vaccine. A mixture of ActHIB (haemophilus b conjugate Vaccine, Tetanus Toxoid Conjugate, Sanofi Pasteur SA) and EG-IM/alum was intramuscularly administered to 6-week-old BALB/c mice (SLC, Japan) three times at intervals of two weeks. Regarding the amount of administration, 2 μg/mouse of ActHIB, 25 μg/mouse of alum or 0.5 μg/mouse of EG-IM was mixed.

2. Measurement of HIB Antigen-Specific Antibody Titers

Two weeks after the last administration, mice were anesthetized, cardiac blood was collected therefrom to prepare a blood sample, and a titer of IgG antibody in blood was measured using a mouse anti-*Haemophilus influenza* type b IgG ELISA kit (XpressBio, USA) in order to measure the titer of HIB antigen-specific antibody.

Figure 8:
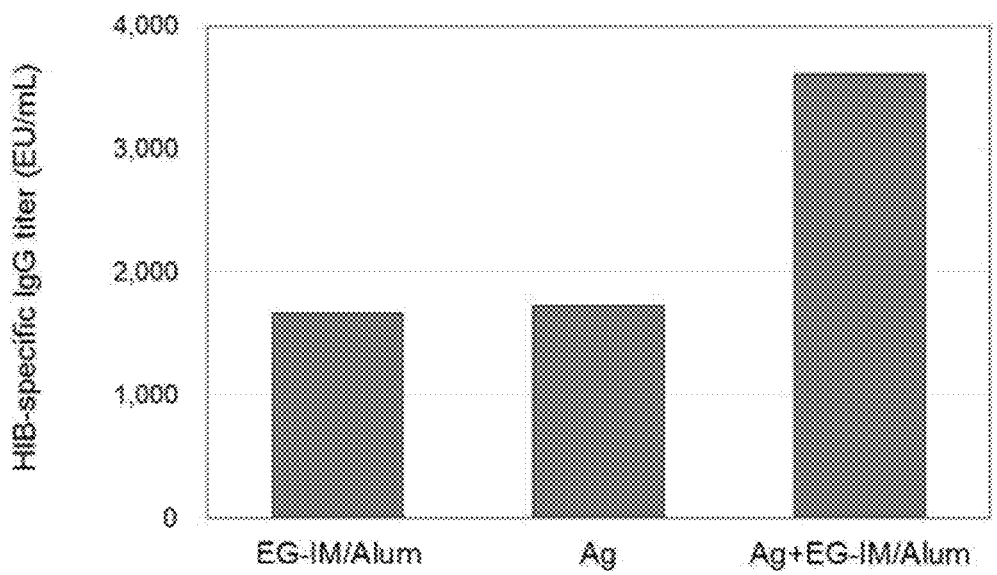
FIG. 8 shows the results of measurement of *Haemophilus influenzae* type b (HIB) antigen-specific antibody titers when using a combination of EG-IM/alum.
Figure 9:
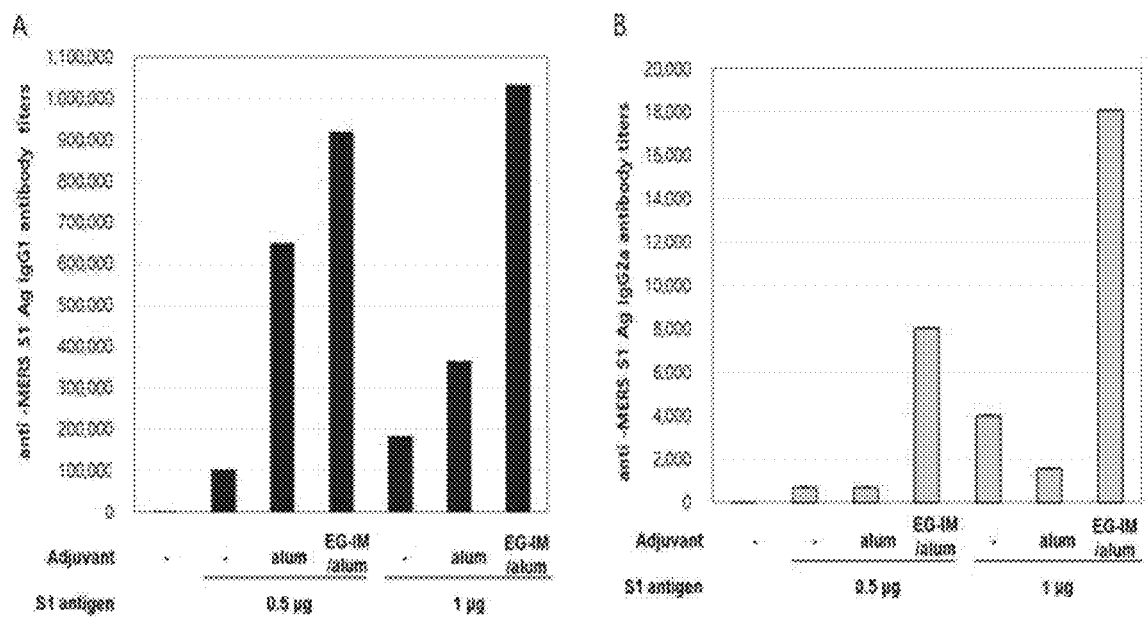
FIG. 9 shows results of measurement of MERS corona Virus (MERS-CoV) spike S1 antigen-specific antibody titers when using a combination of EG-IM/alum, in which graph A shows a MERS virus antigen-specific IgG1 antibody titer in sera and in which graph B shows a MERS virus antigen-specific IgG2a antibody titer in sera.
Figure 10:
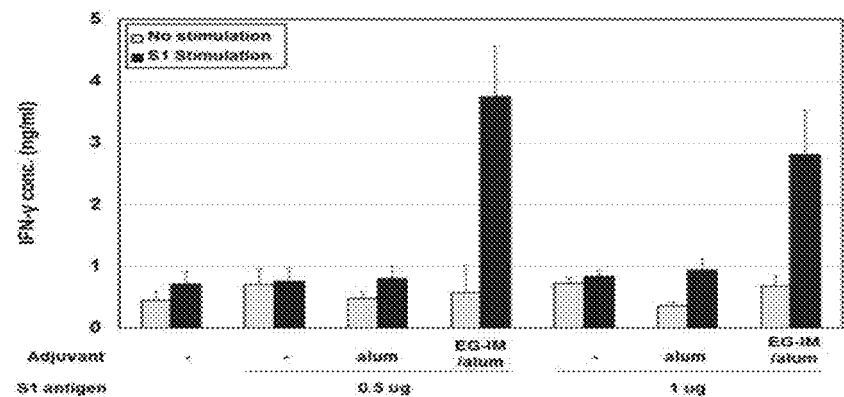
FIG. 10 shows secretion levels of IFN-γ, IL-4 and IL-5 cytokine measured by stimulation with a MERS virus spike S1 protein when administering a MERS vaccine using a recombinant MERS-CoV S1 RBD protein.
Figure 10:
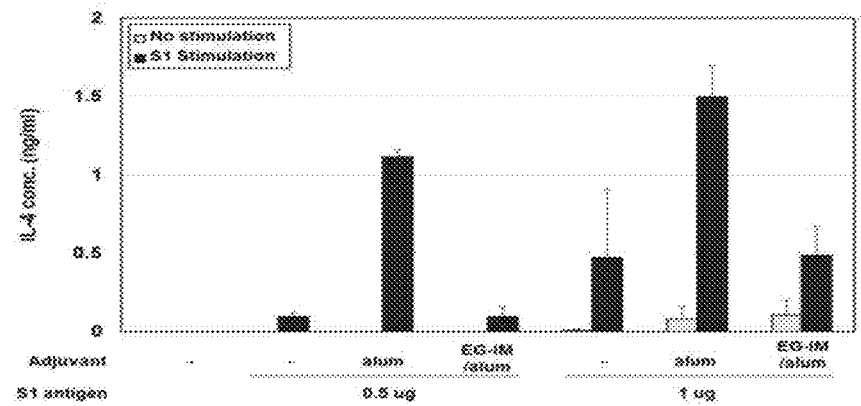
Figure 10:
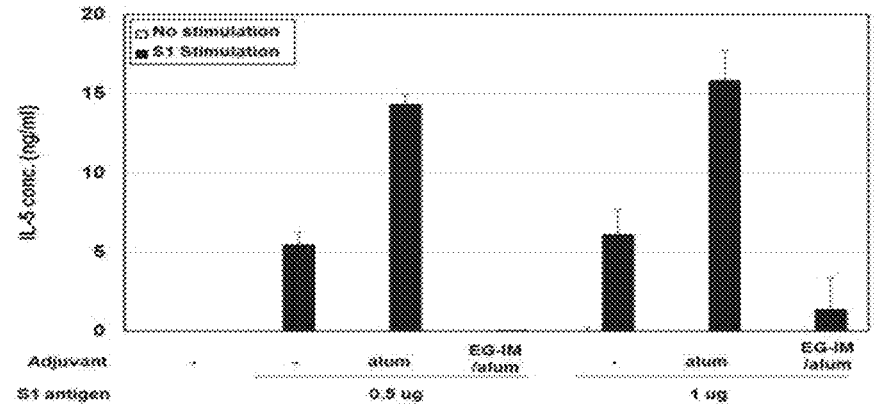

As a result, the test group using EG-IM/alum exhibited 2-fold increase in production of HIB antigen-specific IgG antibody, as compared to a commercially available vaccine (FIG. 8).

Thus, it can be seen that the B-type *Haemophilus influenzae* vaccine containing both EG-IM as an immune modulator as well as alum as an immune adjuvant induces an antibody-mediated immune response and has excellent immunity efficacy, that is, vaccine efficacy.

Example 5: Analysis of Efficacy of EG-IM/Alum in Recombinant Vaccine

<Mers Vaccine>

I. Case of Using Recombinant MERS-CoV Spike S1 Protein

1. Immunization of MERS Vaccine

A recombinant MERS-CoV spike S1 protein (eEnzyme, MERS-S1-005P) was used to identify the immunogenicity enhancement effect of EG-IM/alum in a recombinant vaccine. A mixture of the recombinant MERS-CoV spike S1 protein and alum and/or EG-IM was intramuscularly administered to 6-week-old BALB/c mice (SLC, Japan) three times at intervals of two weeks. Regarding the amount of administration, 0.5 or 1 μg/mouse of the S1 protein, 25 μg/mouse of alum or 0.5 μg/mouse of EG-IM was mixed.

2. Measurement of MERS Virus Antigen-Specific Antibody Titers

Four weeks after the last administration, mice were anesthetized, cardiac blood was collected therefrom to prepare a blood sample, and titers of IgG1 and IgG2a antibodies in blood were measured using an ELISA kit in order to measure the titers of MERS virus antigen-specific antibodies.

As a result, the test group using EG-IM/alum concentration-dependently increased production of MERS virus antigen-specific IgG1 and IgG2a antibodies, as compared to a test group using alum alone and the increment of IgG2a was higher than that of IgG1, as compared to a test group using alum alone (FIG. 9). Thus, it can be seen that the MERS vaccine containing both EG-IM as an immune modulator as well as alum as an immune adjuvant has excellent immunity efficacy, that is, vaccine efficacy.

3. Cytokine Analysis

Four weeks after the final administration, mice were anesthetized, spleen tissues were extracted and separated into single cells, and the cells were stimulated with S1 protein, and cultured for 72 hours. Then, secretion of IFN-γ, IL-4 and IL-5 cytokines was analyzed by sandwich ELISA (R&D systems, DY485; DY404; DY405).

As a result, the test group using EG-IM/alum concentration-dependently enhanced IFN-γ secretion, as compared to the test group using alum alone which functions to improve humoral immunity, but reduced secretion of IL-4 and IL-5 (FIG. 10).

II. Case of Using Recombinant MERS-CoV S1 RBD Protein

1. Immunization of MERS Vaccine

A recombinant MERS-CoV S1 RBD protein was used to identify the immunogenicity enhancement effect of EG-IM/alum in a recombinant vaccine. A mixture of the recombinant MERS-CoV S1 RBD protein, and alum and/or EG-IM was intramuscularly administered to 6-week-old BALB/c mice (SLC, Japan) three times at intervals of two weeks. Regarding the amount of administration, 1 µg/mouse of the RBD protein, 25 µg/mouse of alum, 12.5 µg/mouse of Addavax or 0.5 µg/mouse of EG-IM was mixed.

2. Cytokine Analysis

Two weeks after the final administration, mice were anesthetized, spleen tissues were extracted and separated into single cells, and the cells were stimulated with RBD protein and cultured for 72 hours. Then, in order to analyze a T cell subtype contributing to secretion of IFN-γ cytokine, each test group was treated with a CD4 blocking antibody or CD8 blocking antibody when stimulating with the antigen. After 72 hours, the cell culture solution was collected and secretion of IFN-γ cytokine was analyzed by sandwich ELISA (R&D systems, DY485). AddaVax (Invivogen) was used as a control immune adjuvant.

Figure 11:
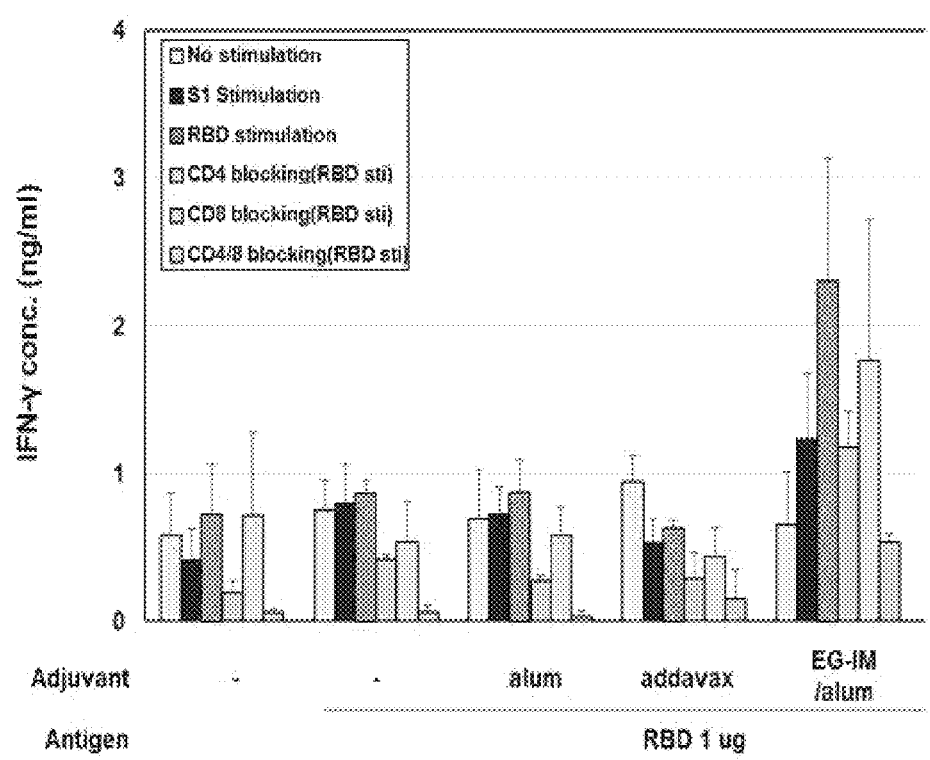
FIG. 11 shows the results of measurement of the secretion level of IFN-γ cytokine when administering a MERS vaccine using the recombinant MERS-CoV spike RBD protein.

As a result, the test group using EG-IM/alum enhanced IFN-γ secretion, as compared to the test group using alum alone which functions to improve humoral immunity, or the test group using addavax (FIG. 11).

Thus, it can be found that the MERS vaccine containing EG-IM and alum has excellent ability to induce TH1-type cellular immunity as well as antibody-mediated immune response.

<Zika Vaccine>

1. Immunization of Zika Vaccine

A recombinant Zika virus envelope protein was used to identify the immunogenicity enhancement effect of EG-IM/alum in a recombinant vaccine. A mixture of a recombinant Zika virus envelope protein, and alum and/or EG-IM was intramuscularly administered to 6-week-old BALB/c mice (SLC, Japan) twice at intervals of two weeks. Regarding the amount of administration, 2 µg/mouse of the Zika virus envelope protein was mixed with 25 µg/mouse of alum or 0.5 µg/mouse of EG-IM.

2. Measurement of Zika Virus Antigen-Specific Antibody Titers

Two weeks after the last administration, mice were anesthetized, cardiac blood was collected therefrom to prepare a blood sample, and titers of IgG1 and IgG2a antibodies in blood were measured using an ELISA kit in order to measure the titers of recombinant Zika virus envelope protein-specific antibodies.

Figure 12:
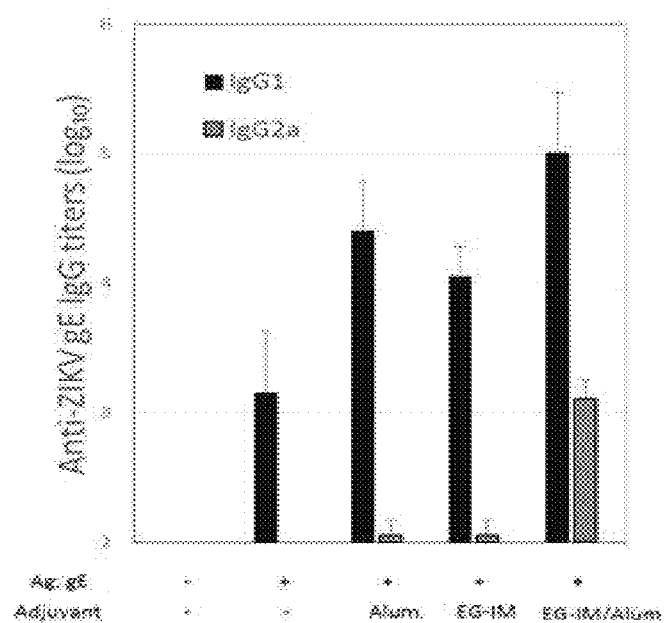
FIG. 12 shows the results of measurement of a Zika virus antigen-specific antibody titer when using a combination of EG-IM/alum.

As a result, the test group using EG-IM/alum improved production of Zika virus antigen-specific IgG1 and IgG2a antibodies, as compared to a test group using EG-IM alone or using alum alone, and the increment of IgG2a was higher than that of IgG1, as compared to a test group using alum alone (FIG. 12). Thus, it can be seen that the Zika vaccine containing both EG-IM as an immune modulator as well as alum as an immune adjuvant has excellent immunity efficacy, that is, vaccine efficacy.

3. Cytokine Analysis

Two weeks after the final administration, mice were anesthetized, spleen tissues were extracted and separated into single cells, and the cells were stimulated with Zika virus envelope protein and cultured for 72 hours. Then, secretion of IFN-γ and IL-5 cytokines was analyzed by sandwich ELISA (R&D systems, DY485; DY405).

Figure 13:
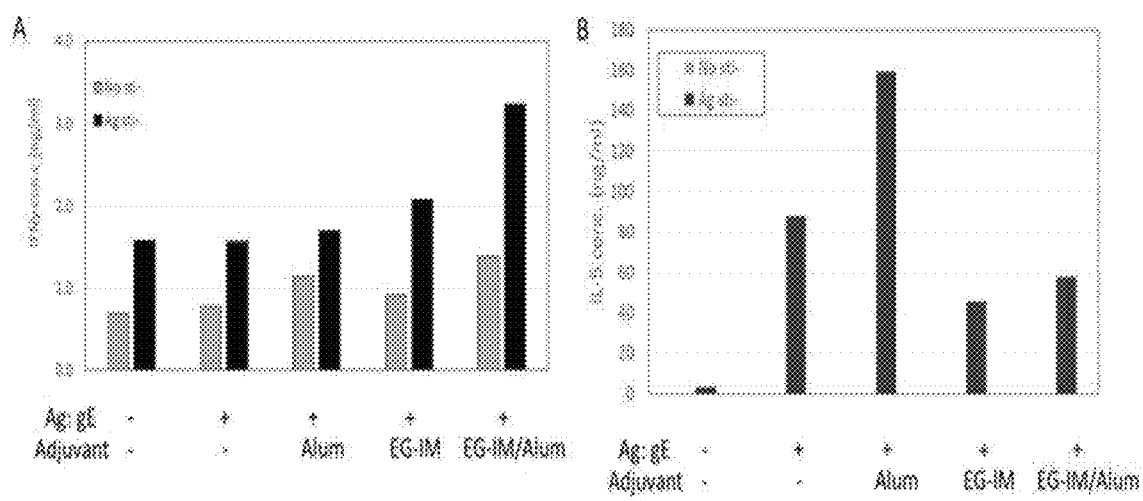
FIG. 13 shows the results of measurement of the secretion levels of IFN-γ and IL-5 cytokines when administering a Zika vaccine.

As a result, the test group using EG-IM/alum concentration-dependently enhanced IFN-γ secretion, as compared to the test group using alum alone which functions to improve humoral immunity, but reduced IL-5 secretion (FIG. 13).

Thus, it can be found that the Zika vaccine containing EG-IM and alum has excellent ability to induce TH1-type cellular immunity as well as antibody-mediated immune response.

Example 6: Analysis of Efficacy of EG-IM/Alum in Extracted Protein Vaccine

1. Immunization of *Pseudomonas aeruginosa* Vaccine

A *P. aeruginosa* FT2 antigen or FT1 antigen was used to identify the immunogenicity enhancement effect of EG-IM/alum in an extracted protein vaccine. A mixture of the FT2 antigen or FT1 antigen, and alum and/or EG-IM was intramuscularly administered to 6-week-old BALB/c mice twice at intervals of one week. The antigen was used in an amount of 5 or 6.5 µg/mouse. A group administered PBS was used as a negative control group.

2. Measurement of *Pseudomonas aeruginosa* Antigen-Specific Antibody Titers

Two weeks after the last administration, mice were anesthetized, cardiac blood was collected therefrom to prepare a blood sample, and titers of (total) IgG, IgG1, IgG2a antibodies in blood were measured using an ELISA kit in order to measure the titers of *Pseudomonas aeruginosa* antigen-specific antibodies.

Figure 14:
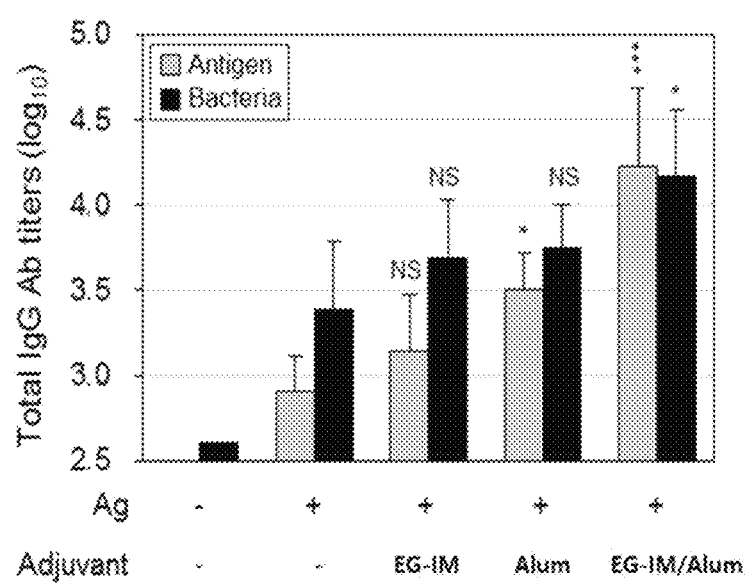
Figure 15:
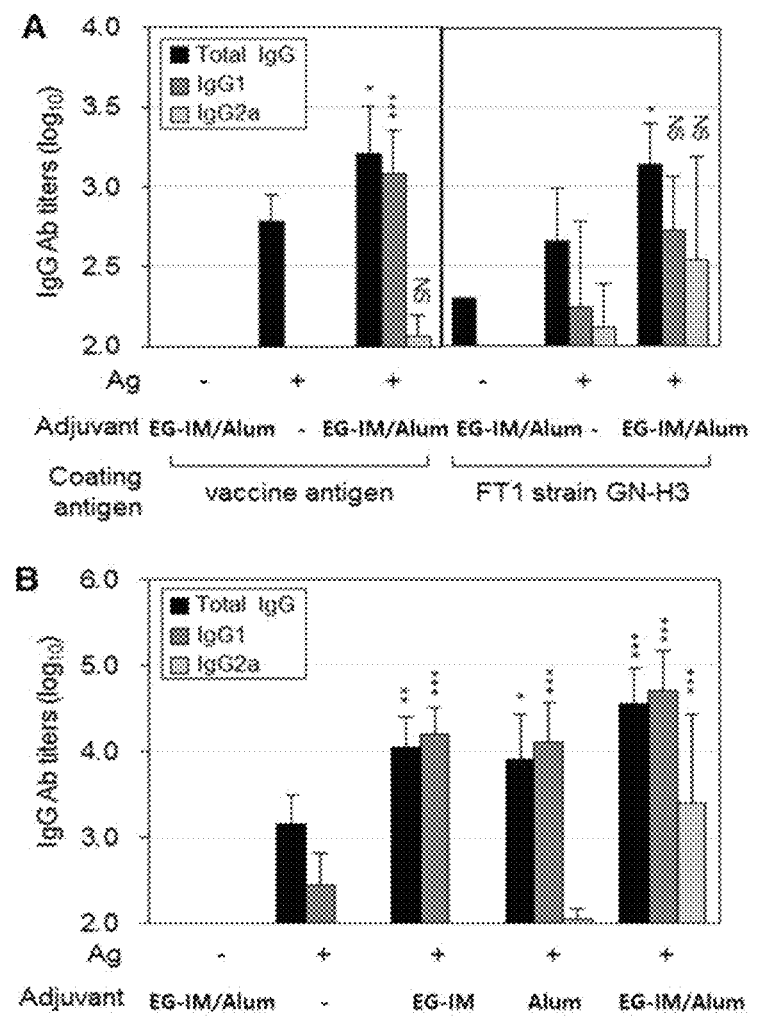

As a result, when immunizing using the *P. aeruginosa* FT2 antigen, the test group using EG-IM/alum improved production of *Pseudomonas aeruginosa*-specific IgG antibodies, as compared to a test group using EG-IM alone or using alum alone (FIG. 14). In addition, when immunizing using the *P. aeruginosa* FT1 antigen, as well, the test group using EG-IM/alum improved production of antigen-specific IgG, IgG1 and IgG2a antibodies as well as production of *P. aeruginosa* GN3 (FT1 strain)-specific IgG, IgG1 and IgG2a antibodies, as compared to a test group using EG-IM alone or using alum alone (FIG. 15). This indicates that the EG-IM/alum used as an immune adjuvant improves reactivity to antigen used for *P. aeruginosa* vaccine as well as reactivity to actual infectious bacteria cells.

3. Measurement of Opsonophagocytic Activity of Mouse Serum Formed by Immunization of *Pseudomonas aeruginosa* Vaccine In order to determine the opsonophagocytic activity of the mouse sera formed by immunization of the *Pseudomonas aeruginosa* vaccine, 6.5 µg of a *P. aeruginosa* FT2 antigen alone or a mixture of the antigen with alum and/or EG-IM was administered twice at intervals of two weeks. Two weeks after the final immunization, cardiac blood was collected, serum was collected and the opsonophagocytic activity against *P. aeruginosa* PA103 (FT2 strain) was measured. Specifically, *P. aeruginosa* FT2 was grown to an exponential phase, collected, heat-inactivated at 56° C. for 30 minutes, and reacted with 100 µg/ml FITC-Isomer I at 4° C. for 1 hour to label the strain with fluorescence. The fluorescence-labeled strain was washed several times with PBS and diluted to an OD600 of 0.9 using a buffer solution for testing opsonophagocytic activity (5% defined FBS and 0.1% gelatin in HBSS). The fluorescence-labeled strain was counted and $5 \times 10^6$ CFU thereof was mixed with immunized serum, mixed with inactivated rabbit complement and cultured with shaking in absence of light for 30 minutes. Then, the strain mixture was mixed with HL-60 cells at a ratio of 20:1 (strain:HL-60 cells) and cultured for 30 minutes. After culture, the cells were washed with PBS containing 0.1% BSA, collected and analyzed using flow cytometry (FACSCanto II™ system, BD Biosciences) and FlowJo software (Treestar, USA). Opsonophagocytic activity was expressed as mean fluorescence intensity (MFI) marked in HL-60 cells.

Figure 16:
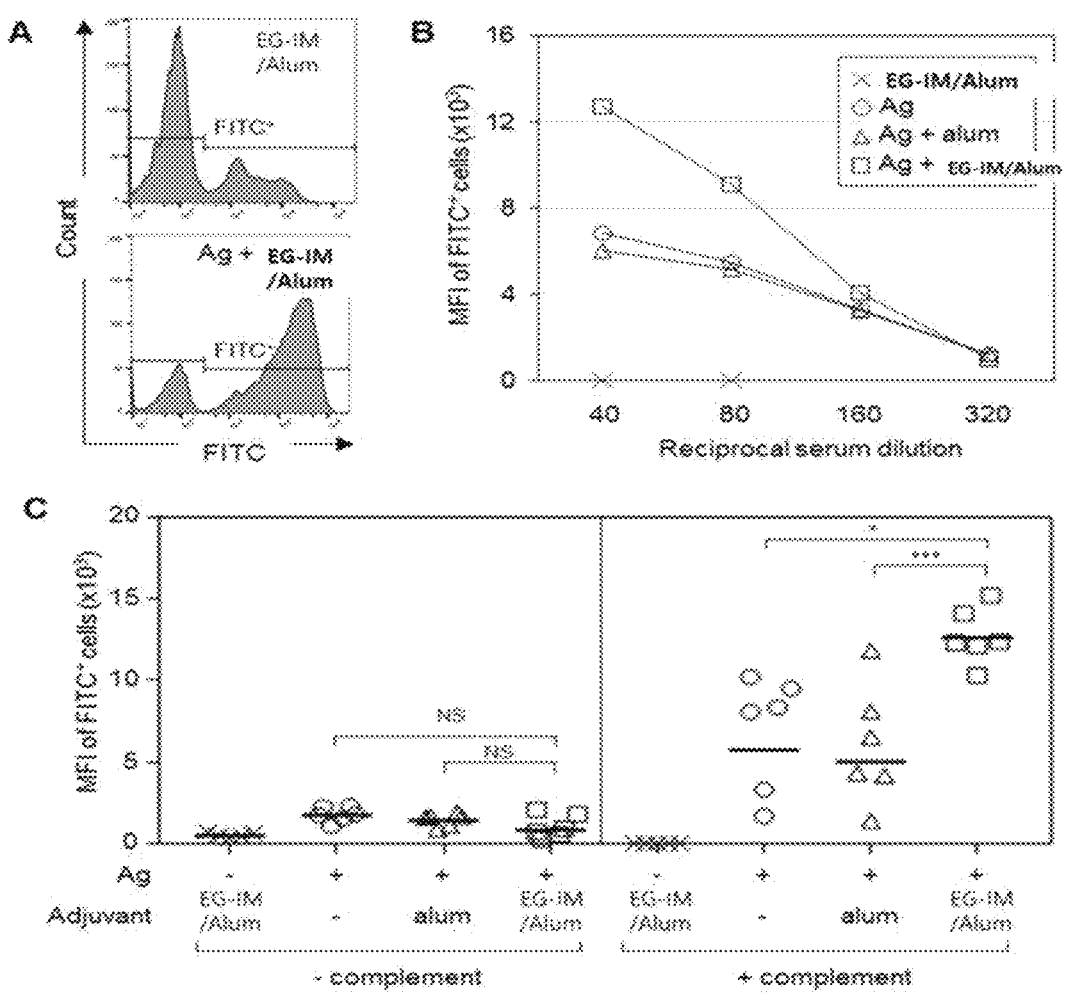
FIG. 16 shows the results of opsonophagocytic activity of mouse sera against *P. aeruginosa* when using a combination of EG-IM/alum. The graphs A show a phagocytic stimulation-inducing activity, the graph B shows a phagocytic stimulation-inducing activity depending on serum concentration, and the graphs C show the results of comparison in phagocytic stimulation activity when lacking a complement and when including a complement.

As a result, phagocytosis was activated by the serum of mouse administered a combination of an antigen and EG-IM/alum, as compared to a negative control group administered EG-IM/alum alone or a test group administered a combination of the antigen and alum (FIG. 16 in graphs A). Phagocytosis was dependent upon serum concentration and complement (FIG. 16, graph B and graphs C). From this, it can be seen that the antibody specific to *Pseudomonas aeruginosa* vaccine induced by the EG-IM/alum composition enhanced opsonophagocytosis against *P. aeruginosa*, so that the functions of the antibody can be improved.

4. Measurement of Protective Efficacy of *P. aeruginosa* Antigen

In order to identify the protective efficacy of EG-IM/alum on *Pseudomonas aeruginosa* antigen, 5 μg of a mixture of a FT2 antigen, and alum and/or EG-IM was administered to 6-week-old BALB/c mice twice at intervals of one week. The group administered PBS was used as a negative control group. Two weeks after the last administration, blood samples were collected and one week later, the mice were lethal challenged with 10 LD50 of *P. aeruginosa* FT2 strain PA103 and survival thereof was observed for 8 days.

TABLE 2

| Immunization | Protective efficacy (%) |
| --- | --- |
| PBS | 0 |
| Ag | 20 |
| Ag + EG-IM | 0 |
| Ag + Alum | 20 |
| Ag + EG-IM/Alum | 80 |

As can be seen from Table 2 above, the test group using EG-IM/alum was induced to have protective efficacy of about 80%. However, the test group using EG-IM or alum alone was almost not induced to have protective efficacy.

Therefore, it is known that a *Pseudomonas aeruginosa* vaccine prepared by mixing a water-soluble protein mixture extracted from *Pseudomonas aeruginosa* as the antigen, EG-IM as an immune modulator, and alum as an immune adjuvant is capable of considerably inducing an antibody-mediated immune response as well as protective efficacy.

INDUSTRIAL APPLICABILITY

The immune modulator of the present invention has excellent immunity enhancement efficacy due to excellent ability to induce both innate immunity and adaptive immune response to a specific pathogen, and is excellent in safety because it has almost no toxicity. In addition, the vaccine containing the immune modulator of the present invention includes both the immune modulator and alum, thereby exhibiting an enhanced immune enhancement effect, as compared to the case where the immune modulator is used alone.

The invention claimed is:

1. An immune modulator represented by the following Formula 1:

[Formula 1]

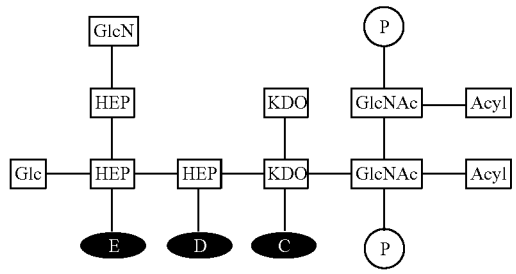

wherein Glc is glucose, GlcN is glucosamine, HEP is heptose, KDO is 2-keto-3-deoxy-octonate, GlcNAc is N-acetylglucosamine, P is phosphate, and C to E are positions to which phosphates can be bonded, wherein each phosphate is bonded at a position selected from the group consisting of C, E, CD, CE, DE, and CDE of Formula 1, wherein the immune modulator is detoxified by deacylating lipid A through treatment of lipooligosaccharide (LOS) with an alkali.

2. The immune modulator according to claim 1, wherein the number of the phosphates is 2 to 5.

3. The immune modulator according to claim 1, wherein the immune modulator has no O-linked fatty acid.

4. The immune modulator according to claim 1, wherein the immune modulator has immunostimulatory activity.

5. An immune adjuvant composition comprising the immune modulator according to claim 1 and an immune adjuvant ingredient selected from the group consisting of: a Group II element selected from the group consisting of Mg, Ca, Sr, Ba and Ra, or a salt thereof; a Group IV element selected from the group consisting of Ti, Zr, Hf and Rf; an aluminum salt or hydrate thereof; and dimethyloctadecylammonium bromide.

6. A vaccine composition comprising:
(a) an antigen;
(b) the immune modulator according to claim 1; and
(c) alum.

7. The vaccine composition according to claim 6, wherein the antigen is selected from the group consisting of a peptide, a protein, a nucleic acid, a sugar, a pathogen, an attenuated pathogen, an inactivated pathogen, a virus, a virus-like particle (VLP), a cell or a cell fragment.

8. The vaccine composition according to claim 6, wherein the antigen is selected from the group consisting of an antigen of Japanese encephalitis virus, an antigen of *Haemophilus influenzae* type B (HIB), an antigen of Middle East Respiratory Syndrome (MERS) virus, an antigen of Zika virus, an antigen of *Pseudomonas aeruginosa*, an antigen of pertussis, an antigen of *Mycobacterium tuberculosis*, an antigen of *Bacillus* anthrax, an antigen of hepatitis A virus (HAV), an antigen of hepatitis B virus (HBV), an antigen of hepatitis C virus (HCV), an antigen of human immunodeficiency virus (HIV), an antigen of herpes simplex virus (HSV), an antigen of *Neisseria meningitidis*, an antigen of *Corynebacterium diphtheria*, an antigen of *Bordetella pertussis*, an antigen of *Clostridium tetani*, an antigen of human papilloma virus (HPV), an antigen of Varicella virus, an antigen of Enterococci, an antigen of *Staphylococcus aureus*, an antigen of *Klebsiella pneumoniae*, an antigen of *Acinetobacter baumannii*, an antigen of *Enterobacter*, an antigen of *Helicobacter pylori*, an antigen of *Plasmodium* spp., an antigen of a dengue virus, an antigen of *Orientia tsutsugamushi*, an antigen of severe fever with thrombocytopenia syndrome Bunyavirus (SFTS Bunyavirus), an antigen of severe acute respiratory syndrome-coronavirus (SARS-CoV), an antigen of an influenza virus, an antigen of an Ebola virus and an antigen of *Diplococcus pneumoniae*.

9. The vaccine composition according to claim 6, wherein the vaccine is an inactivated vaccine, an attenuated vaccine, a subunit vaccine, a recombinant vaccine, a protein-conjugated vaccine, a monovalent vaccine, a multivalent vaccine, or a mixed vaccine.

\* \* \* \* \*